(12) United States Patent
Balli

(10) Patent No.: US 7,824,615 B2
(45) Date of Patent: Nov. 2, 2010

(54) SUPPORT ELEMENT FOR TEST-TUBES AND THE LIKE

(75) Inventor: Lorenzo Balli, Signa (IT)

(73) Assignee: Everex S.R.L., Sesto Fiorentino (Firenze) (IT)

( * ) Notice: Subject to any disclaimer, the term of this patent is extended or adjusted under 35 U.S.C. 154(b) by 718 days.

(21) Appl. No.: 11/658,708

(22) PCT Filed: Jul. 27, 2005

(86) PCT No.: PCT/IT2005/000447

§ 371 (c)(1), (2), (4) Date: Jan. 29, 2007

(87) PCT Pub. No.: WO2006/011178

PCT Pub. Date: Feb. 2, 2006

(65) Prior Publication Data

US 2008/0317641 A1    Dec. 25, 2008

(30) Foreign Application Priority Data

Jul. 30, 2004    (IT) ............................ FI2004A0170

(51) Int. Cl.
*G01N 35/02* (2006.01)
*G01N 35/04* (2006.01)

(52) U.S. Cl. ............................ 422/65; 422/63; 422/64; 422/66

(58) Field of Classification Search .............. 422/63–66
See application file for complete search history.

(56) References Cited

U.S. PATENT DOCUMENTS

| | | | | |
|---|---|---|---|---|
| 3,730,331 | A | * | 5/1973 | Goldberg ..................... 198/793 |
| 4,634,575 | A | * | 1/1987 | Kawakami et al. ............ 422/63 |
| 5,019,243 | A | | 5/1991 | McEwen et al. |
| 5,397,542 | A | | 3/1995 | Nelms et al. |
| 5,651,941 | A | | 7/1997 | Stark et al. |
| 2003/0133848 | A1 | * | 7/2003 | Itoh ........................... 422/104 |

FOREIGN PATENT DOCUMENTS

| | | |
|---|---|---|
| EP | 0 414 644 A2 | 2/1991 |
| EP | 0 469 390 A2 | 2/1992 |
| WO | 2005/039767 A2 | 5/2005 |

* cited by examiner

*Primary Examiner*—Jill Warden
*Assistant Examiner*—Paul S Hyun
(74) *Attorney, Agent, or Firm*—The Webb Law Firm

(57) ABSTRACT

A support element for test-tubes and the like, including an annular body adapted to be fitted on a test-tube and provided with connection means among several support elements to allow the formation of a chain having additional support elements, wherein the connection means are a spherical joint.

4 Claims, 6 Drawing Sheets

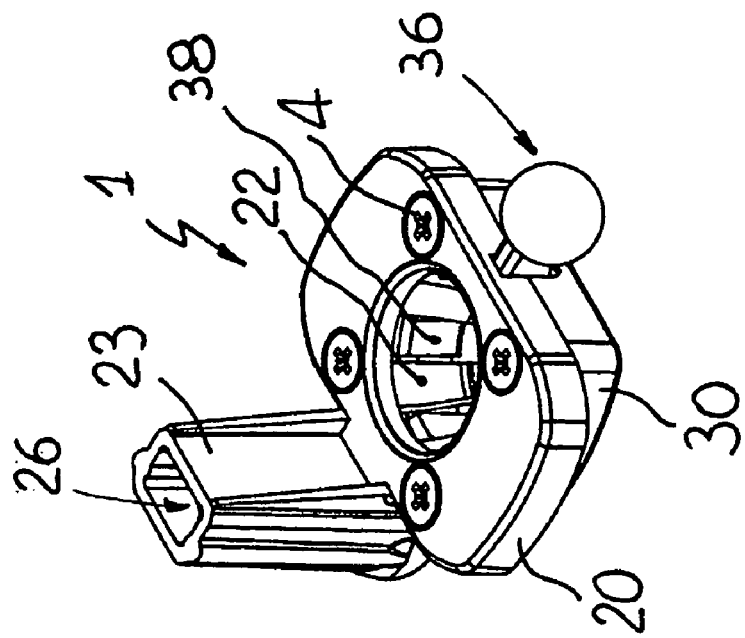
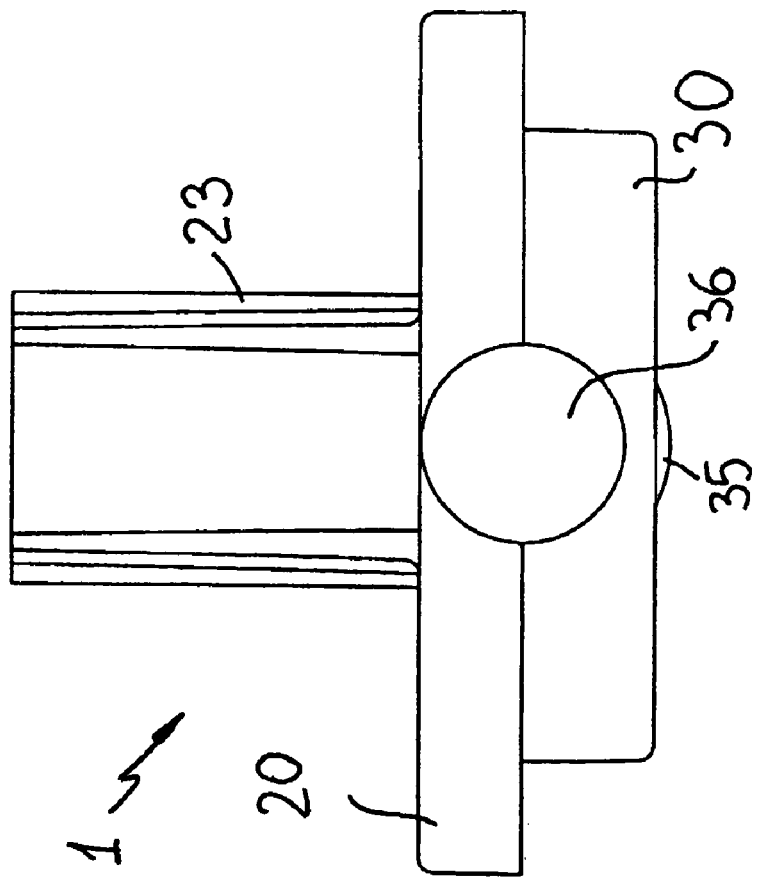

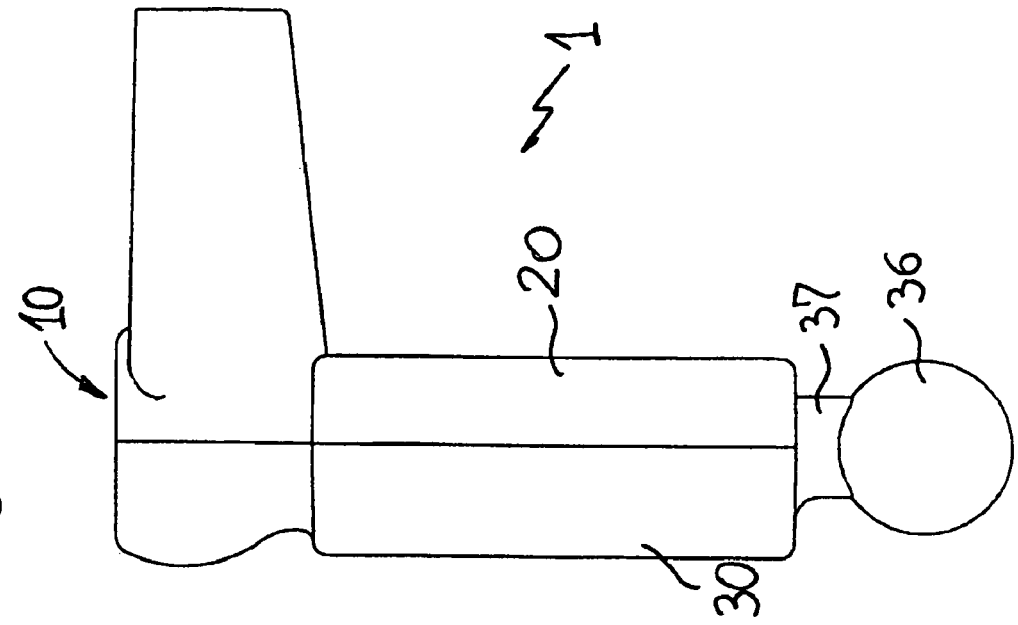
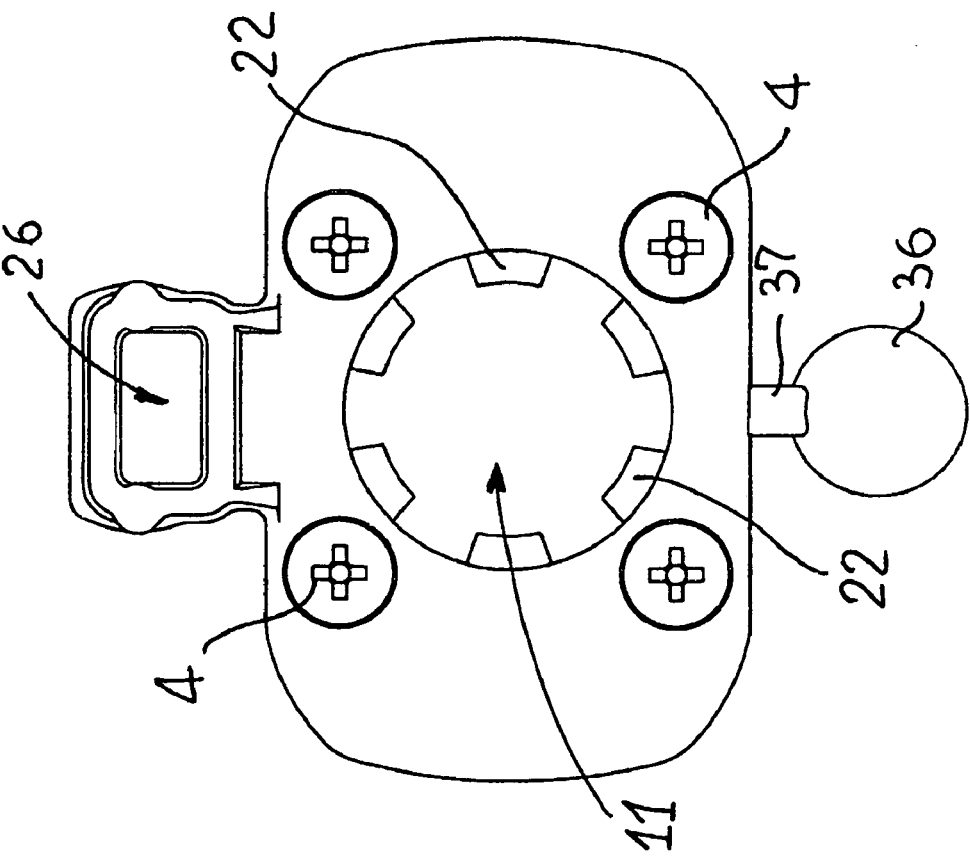

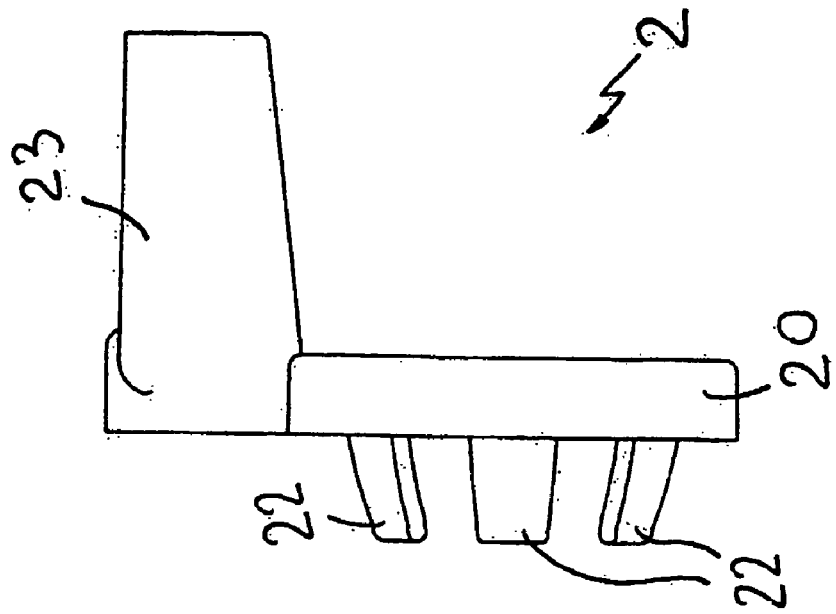
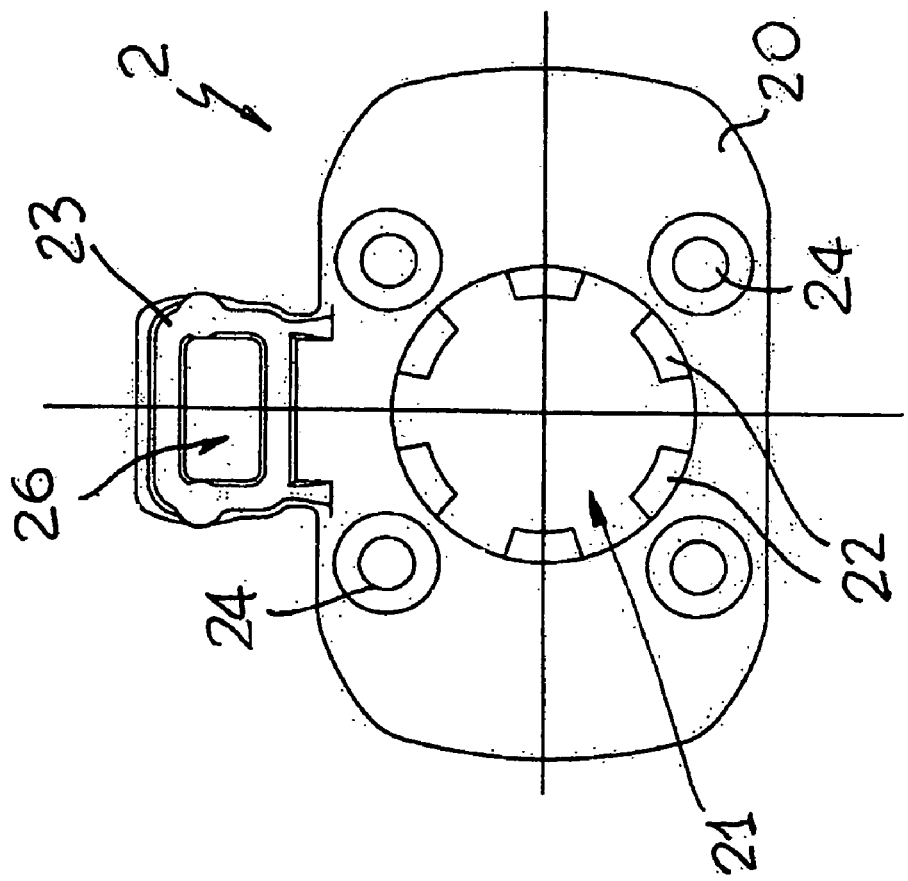
Fig. 7
Fig. 8

SUPPORT ELEMENT FOR TEST-TUBES AND THE LIKE

CROSS-REFERENCE TO RELATED APPLICATIONS

This application is a National Stage Application under 35 U.S.C. §371 of International Application PCT/IT2005/000447, filed Jul. 27, 2005, which claims priority to Italian Application No. FI2004A000170, filed Jul. 30, 2004.

BACKGROUND OF THE INVENTION

1. Field of the Invention

The present invention relates to a support element for test-tubes and the like.

2. Description of Related Art

The use of support elements for test-tubes is well known, said elements being formed by annular bodies apt to be fitted on the test-tubes and provided with connecting means which allow the connection thereof, thus forming chains including a plurality of said elements.

The chains of support elements so formed determinate the formation of chains of corresponding test-tubes, which can be stored, transported and handled in groups of many elements.

Using the support elements of known type, it isn't possible to execute some movements of the test-tubes joined in chains, as, for example, the movements required when some types of examinations must be executed. In particular, it is impossible to swing or to turn over a test-tube of the chain. This obliges to release the test-tube to be submitted to a swinging movement from the chain and, thus, to utilize singularly the test-tube, eliminating the advantages deriving from the joining of the test-tubes in chains.

SUMMARY OF THE INVENTION

The main aim of the present invention is to eliminate the above mentioned drawbacks.

This result has been achieved according to the invention thanks to the idea of producing a support element for test-tubes having the features described in the claims. Other features relate to the dependent claims.

Thanks to the present invention, it is possible to move each test-tube being a part of the chain, executing revolutions of the same test-tube, allowing to execute shaking and/or turning over the same test-tube without detaching the test-tube from the chain which contain it; that a chain thus formed can be moved along curves in the space; that it is possible to obtain a release mounting of the support elements, easily forming chains of any desired length: that each support element can receive an identifying device, like a transponder, apt to provide data about the patient, about the kind of examination to be executed, about the position of the test-tube, etc.; that the support elements, and also the chains formed by the same, have a structural resistance which maintains unaltered their features even after a prolonged use.

These and other advantages and characteristics of the invention will be best understood by anyone skilled in the art from a reading of the following description in conjunction with the attached drawings given as a practical exemplification of the invention, but not to be considered in a limitative sense.

BRIEF DESCRIPTION OF THE DRAWINGS

FIGS. 1, 2, 3 and 4 relate to a possible example of a support element for test-tubes according to the present invention, represented in different scales, respectively, in a perspective view (FIG. 1), in a frontal view (FIG. 2), in a plan view (FIG. 3) and in a side view (FIG. 4);

FIGS. 5, 6, 7 and 8 relate to a part of the support element of FIGS. 1-4, represented in different scales, respectively, in a perspective view (FIG. 5), in a rear view (FIG. 6), in a plan view (FIG. 7) and in side view (FIG. 8)

DETAILED DESCRIPTION OF THE PREFERRED EMBODIMENTS

Figure 5:
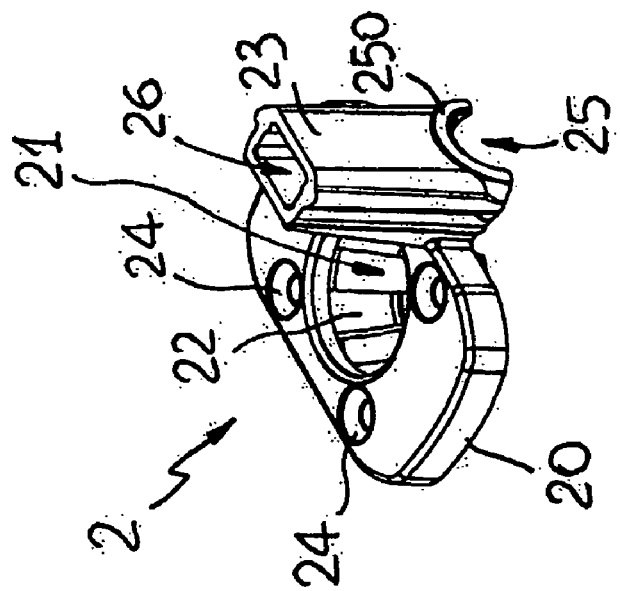
Figure 6:
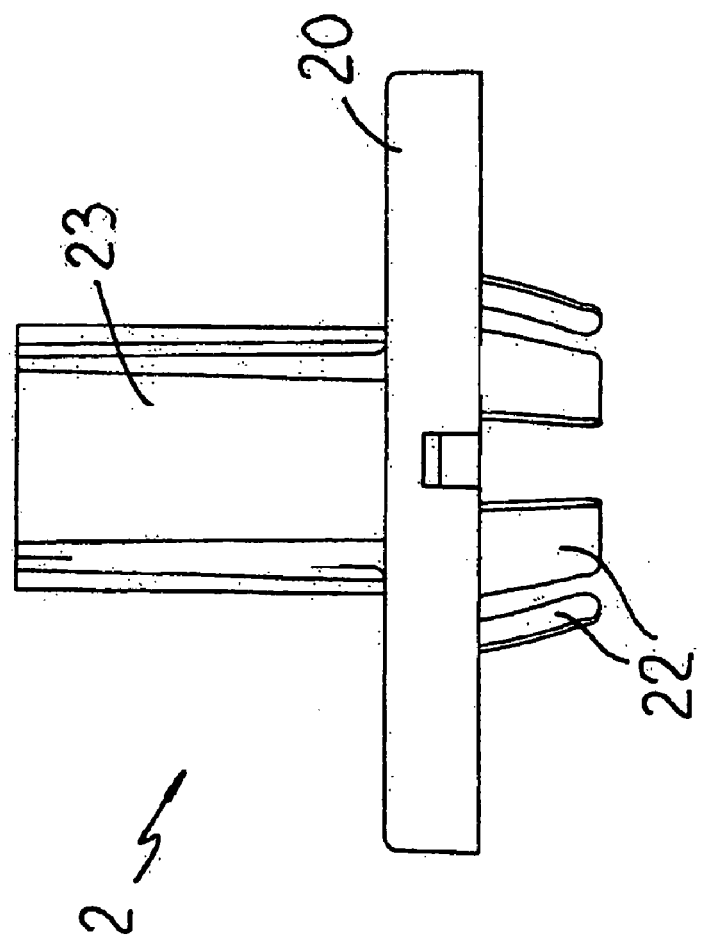
Figure 9:
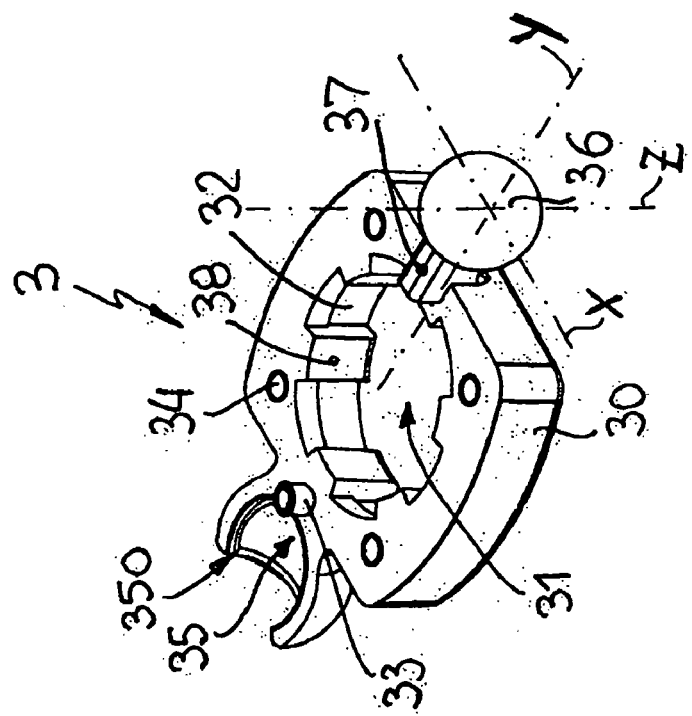
FIGS. 9, 10, 11 and 12 relate to another part of the support element of FIGS. 1-4, represented in different scales, respectively, in a perspective view (FIG. 9), in a front view (FIG. 10), in a plan view (FIG. 11) and in a side view (FIG. 12).
Figure 10:
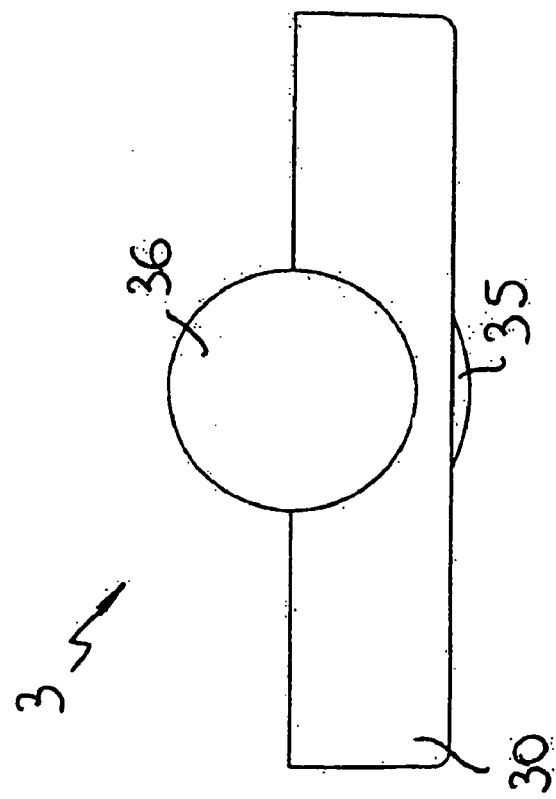
Figure 12:
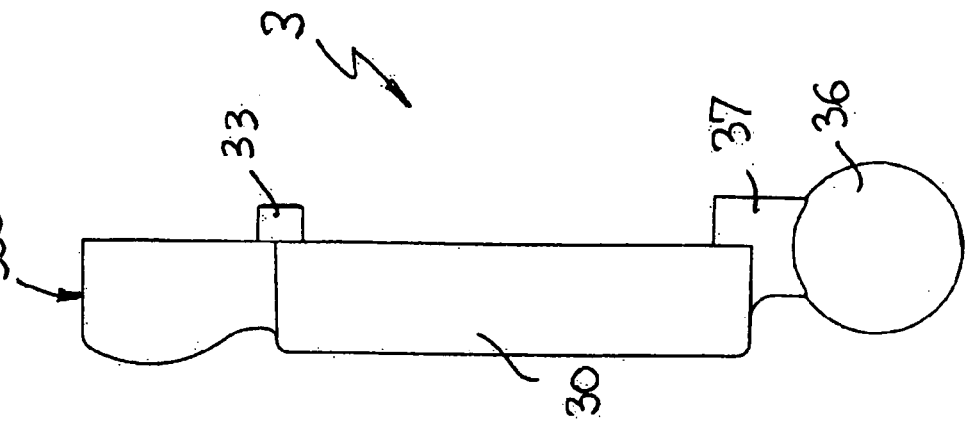
Figure 11:
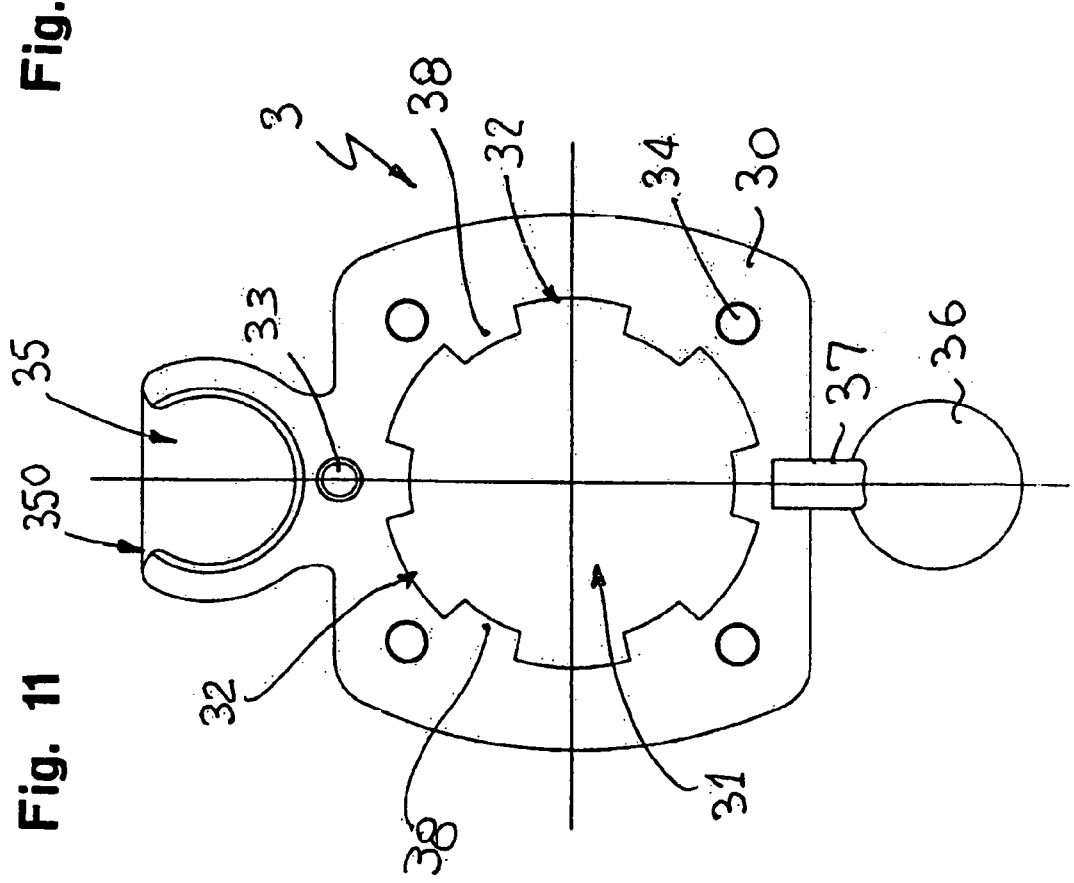

According to the present invention, a support element 1 for test-tubes and the like is of the type formed by an annular body apt to be fitted on the test-tube and provided with connection means among several support elements to allow the formation of a chain of more elements: said connection means (10, 36) forming a spherical joint allowing the rotation of the supported test-tube about three orthogonal axes (x, y, z). In particular, the body of the element 1 is formed by two portions or semi-shells 2 and 3 which in the example are reciprocally bound by screws 4.

The superior semi-shell 2 is constituted by a body 20 having a rounded rectangular plant, provided with a central passing hole 21. Around the circumference of the hole 21 there is a plurality of thin plates or tabs 22. Said tabs 22 are elastically yielding, angularly equidistant around said hole, with their free ends downwardly and slightly centripetally inclined. On the body 20 of the semi-shell 2, there are four passing seats 24 for said screws 4.

On a side of the body 20 there is an appendix 23, which is hollow so as to define a vertical seat 26. The seat 26 can be used for the housing of an identification device as, for example, a transponder. The identification device can univocally identify the position of the single support element 1 in the chain and the relative test-tube/patient code. In other words, with the transponder, each sample to be analysed is identified and located in a chain of more elements.

The chain itself is not shown in the drawings. The transponder is per se known and it is not shown in the drawings.

The appendix 23 has a lower semi-seat 25, substantially semi-spherical shaped, open toward the bottom and the outside, i.e. with its concavity turned downwardly.

The lower semi-shell 3 of the element 1 is constituted by a body 30 having a rounded rectangular plant, corresponding to the shape of the semi-shell 2. On the body 30 of the semi-shell 3 there are four seats 34 for the screws 4, disposed correspondingly to the seats 24 of the semi-shell 2 when the two semi-shells are coupled. Besides, on the lower semi-shell 3 there is a pivot 33 which is insertable in a corresponding seat (not visible) of the lower face of the superior semi-shell 2. In practice, the pivot 33 can be used to make easier the correct positioning of the two semi-shells, while the screws 4 determine the stable fixing thereof.

Around the hole 31 there is a plurality of grooves 32, angularly equidistant, disposed in positions corresponding to those of the thin plates or tabs 22. In practice, the grooves 32 are separated by teeth 38 and, when the two semi-shells 2 and 3 are reciprocally associated, they receive the tabs 22. The discontinuous circumference defined by the tabs 22 corresponds, substantially, to the diameter of the test-tube to be received; in this way, the elastic reaction of the tabs 22 allows, when the element 1 is assembled, the test-tube insertion and his stable holding in the seat 11 defined by the holes 21 and 32 of two semi-shells. The lower semi-shell 3, on its side destined to be coupled with the portion which supports the appendix 23 of the semi-shell 2, is provided with one semi-seat 35, having a substantially semi-spherical shape, which is open upwardly and on its outer side.

When the element 1 is assembled, the two semi-seats 25 e 35 are coupled and define a substantially spherical seat 10, having a circular inlet opening defined by the two edges 250 e 350 of the two semi-seats 25 e 35. The semi-shell 3 has a spherical appendix 36, connected to its body 30 by a spacer 37, said spherical appendix 36 being disposed opposite in respect to the semi-seat 35. The diameter of the spherical appendix 36 is such that the same appendix 36 can be inserted/disconnected by forcing it with a slight pressure into/from the spherical seat 10 defined by the two joined semi-bodies 25 and 35. The realization in plastic material of the element 1 contributes to facilitate the association among many elements and, therefore, to quickly vary the number of elements forming the chain.

At the same time, the spherical joint defined by the spherical appendix 36 and by the spherical seat 10 allows to move the test-tube supported by an element of the chain in a plurality of directions in the space. Particularly, as said above, any revolution movement of the test-tube is possible, with the possibility to provide shaking and/or turning over of the single test-tube during an examination.

Clearly, changes may be made to the form, dimensions, component part locations, and type of materials employed in the embodiment described and illustrated herein without, however, departing from the scope of the present invention.

The invention claimed is:

1. A support element for test-tubes and the like, comprising an annular body adapted to be fitted on a test-tube and provided with connection means among several support elements to allow the formation of a chain comprising additional support elements, wherein
   (i) the connection means are a spherical joint comprising a spherical seat and a spherical appendix;
   (ii) the support element is formed by two coupled semi-shells, each of the coupled semi-shells being provided with a substantially semi-spherical shaped semi-seat, the semi-seats forming the spherical seat when the two semi-shells are coupled wherein the two coupled semi-shells further comprise corresponding seats defining a receiving seat when the element is assembled, said receiving seat being delimited by a plurality of elastically yielding tabs for stably receiving a test tube; and
   (iii) the semi-seats are delimited by corresponding semi-circular edges defining an inlet opening of the spherical seat when the support element is assembled.

2. The support element according to claim 1, wherein the diameter of the opening defined by the edges of the semi-seats corresponds to the diameter of the spherical appendix.

3. The support element according to claim 1, wherein one of the semi-shells includes the plurality of elastically yielding tabs delimiting the receiving seat.

4. The support element according to claim 1, further comprising a seat for receiving an identifying device.

* * * * *